United States Patent
Ganske et al.

(10) Patent No.: US 8,764,789 B2
(45) Date of Patent: Jul. 1, 2014

(54) SYSTEM FOR PERFORMING REMOTE ISCHEMIC CONDITIONING

(75) Inventors: Rocky Ganske, Ontario (CA); Lahav Gil, Toronto (CA); Adam Shepperdley, Toronto (CA); Raymond Cracauer, Beulah, CO (US); Igal Royblat, Richmond HIll (CA); Kristopher Thomas Christensen, Oakville (CA); Rade Gadzic, Toronto (CA); Christopher Caldarone, Toronto (CA); Andrew Redington, Toronto (CA)

(73) Assignee: CellAegis Devices Inc., Toronto (CA)

( * ) Notice: Subject to any disclaimer, the term of this patent is extended or adjusted under 35 U.S.C. 154(b) by 307 days.

(21) Appl. No.: 13/088,243

(22) Filed: Apr. 15, 2011

(65) Prior Publication Data

US 2012/0265240 A1 Oct. 18, 2012

(51) Int. Cl.
*A61B 5/0205* (2006.01)
*A61B 17/135* (2006.01)

(52) U.S. Cl.
USPC .......................... 606/202; 600/485; 600/492

(58) Field of Classification Search
USPC ........... 606/201–204; 600/490–496, 500–503
See application file for complete search history.

(56) References Cited

U.S. PATENT DOCUMENTS

| | | |
|---|---|---|
| 3,552,383 A | 1/1971 | Krueger et al. |
| 4,106,002 A | 8/1978 | Hogue, Jr. |
| 4,206,764 A | 6/1980 | Williams |
| 4,321,929 A | 3/1982 | Lemelson et al. |
| 4,664,651 A | 5/1987 | Weinshenker et al. |
| 4,690,151 A | 9/1987 | Utsunomiya et al. |
| 4,967,758 A | 11/1990 | Masciarotte |
| 5,072,736 A | 12/1991 | Ogawa et al. |
| 5,135,003 A | 8/1992 | Souma |
| 5,201,758 A | 4/1993 | Glover |
| 5,267,565 A | 12/1993 | Beard et al. |
| 5,569,304 A | 10/1996 | Ulrich |
| 5,571,075 A | 11/1996 | Bullard et al. |
| 5,634,467 A | 6/1997 | Nevo |
| 5,643,315 A | 7/1997 | Daneshvar |
| 5,651,369 A | 7/1997 | Tomita |
| 6,152,881 A | 11/2000 | Raines et al. |
| 6,210,423 B1 | 4/2001 | Kim et al. |

(Continued)

FOREIGN PATENT DOCUMENTS

| | | |
|---|---|---|
| CN | 20082012363 | 11/2008 |
| EP | 0 960 598 A1 | 12/1999 |

(Continued)

OTHER PUBLICATIONS

Search Report from PCT Application No. PCT/US2012/033442, Jun. 12, 2012.

(Continued)

*Primary Examiner* — Kathleen Holwerda
(74) *Attorney, Agent, or Firm* — Wolf, Greenfield & Sacks, P.C.

(57) ABSTRACT

A system for performing remote ischemic conditioning includes an inflatable cuff configured to encircle a limb of a subject and a controller removably attached to the cuff. The controller includes a pump; a manifold in fluid communication with the pump; a connector in fluid communication with the manifold and in removable fluid communication with the inflatable cuff; a pressure sensor; and a control circuit configured to implement a remote ischemic conditioning treatment protocol.

2 Claims, 7 Drawing Sheets

(56) References Cited

U.S. PATENT DOCUMENTS

| | | | |
|---|---|---|---|
| 6,245,023 B1 | 6/2001 | Clemmons | |
| 6,251,080 B1 * | 6/2001 | Henkin et al. | 600/490 |
| 6,344,025 B1 * | 2/2002 | Inagaki et al. | 600/490 |
| 6,485,429 B2 | 11/2002 | Forstner | |
| 6,550,482 B1 | 4/2003 | Burbank et al. | |
| 6,626,840 B2 | 9/2003 | Drzewiecki et al. | |
| 6,702,720 B2 | 3/2004 | Dardik | |
| 6,719,704 B2 | 4/2004 | Narimatsu et al. | |
| 6,858,012 B2 | 2/2005 | Burns et al. | |
| 6,905,456 B1 * | 6/2005 | Brunner et al. | 600/16 |
| 6,962,599 B2 | 11/2005 | Hui et al. | |
| 7,004,907 B2 | 2/2006 | Banet et al. | |
| 7,018,335 B2 | 3/2006 | Kario et al. | |
| 7,048,702 B2 | 5/2006 | Hui | |
| 7,111,346 B2 | 9/2006 | Inman et al. | |
| 7,166,077 B2 | 1/2007 | Millay et al. | |
| 7,228,576 B2 | 6/2007 | Inman et al. | |
| 7,314,478 B2 | 1/2008 | Hui | |
| 7,338,410 B2 | 3/2008 | Dardik et al. | |
| 7,374,540 B2 | 5/2008 | Schnall et al. | |
| 7,390,303 B2 | 6/2008 | Dafni | |
| 7,404,221 B2 | 7/2008 | Sackner | |
| 7,427,268 B2 | 9/2008 | Millay et al. | |
| 7,485,131 B2 | 2/2009 | Hovanes et al. | |
| 7,689,286 B2 | 3/2010 | Pastore et al. | |
| 7,717,855 B2 | 5/2010 | Caldarone et al. | |
| 7,885,710 B2 | 2/2011 | Sih et al. | |
| 8,114,026 B2 * | 2/2012 | Leschinsky | 600/490 |
| 8,246,548 B2 | 8/2012 | Naghavi | |
| 2001/0029389 A1 | 10/2001 | Kim et al. | |
| 2003/0013974 A1 | 1/2003 | Natarajan et al. | |
| 2003/0065270 A1 | 4/2003 | Raines et al. | |
| 2003/0176795 A1 | 9/2003 | Harris et al. | |
| 2003/0216651 A1 | 11/2003 | Burns et al. | |
| 2003/0233118 A1 | 12/2003 | Hui | |
| 2004/0044290 A1 | 3/2004 | Ward et al. | |
| 2004/0064076 A1 | 4/2004 | Bilgi et al. | |
| 2004/0102818 A1 | 5/2004 | Hakky et al. | |
| 2004/0241634 A1 | 12/2004 | Millis et al. | |
| 2004/0255956 A1 | 12/2004 | Vinten-Johansen | |
| 2005/0004476 A1 | 1/2005 | Payvar et al. | |
| 2005/0070405 A1 | 3/2005 | Egger | |
| 2005/0159640 A1 | 7/2005 | Barbut et al. | |
| 2005/0171444 A1 | 8/2005 | Ono et al. | |
| 2005/0177078 A1 | 8/2005 | Loeb et al. | |
| 2006/0052712 A1 | 3/2006 | Poliac et al. | |
| 2006/0052713 A1 | 3/2006 | Poliac et al. | |
| 2006/0052714 A1 | 3/2006 | Poliac et al. | |
| 2006/0058717 A1 | 3/2006 | Hui et al. | |
| 2006/0100639 A1 | 5/2006 | Levin et al. | |
| 2006/0142663 A1 | 6/2006 | Sawanoi et al. | |
| 2007/0005106 A1 | 1/2007 | Adducci | |
| 2007/0055188 A1 | 3/2007 | Avni et al. | |
| 2007/0135836 A1 | 6/2007 | McEwen et al. | |
| 2007/0150005 A1 | 6/2007 | Sih et al. | |
| 2007/0247304 A1 | 10/2007 | Bonnefin et al. | |
| 2008/0077176 A1 * | 3/2008 | Hanlon et al. | 606/201 |
| 2008/0139949 A1 | 6/2008 | Caldarone et al. | |
| 2008/0222769 A1 | 9/2008 | Natonson et al. | |
| 2009/0036785 A1 | 2/2009 | Danielsson | |
| 2009/0124912 A1 | 5/2009 | McEwen et al. | |
| 2009/0137884 A1 | 5/2009 | Naghavi et al. | |
| 2009/0287069 A1 | 11/2009 | Naghavi et al. | |
| 2009/0318818 A1 | 12/2009 | Whitaker et al. | |
| 2009/0324748 A1 | 12/2009 | Dobson | |
| 2010/0081941 A1 | 4/2010 | Naghavi et al. | |
| 2010/0081977 A1 | 4/2010 | Vess | |
| 2010/0105993 A1 | 4/2010 | Naghavi et al. | |
| 2010/0160799 A1 | 6/2010 | Caldarone et al. | |
| 2010/0185220 A1 | 7/2010 | Naghavi et al. | |
| 2010/0186752 A1 | 7/2010 | Rixson | |
| 2010/0268130 A1 | 10/2010 | Khan | |
| 2010/0292619 A1 | 11/2010 | Redington et al. | |
| 2010/0305607 A1 | 12/2010 | Caldarone et al. | |
| 2010/0322467 A1 | 12/2010 | Reed et al. | |
| 2010/0324429 A1 * | 12/2010 | Leschinsky | 600/493 |
| 2010/0328142 A1 | 12/2010 | Zoughi et al. | |
| 2011/0077566 A1 | 3/2011 | Ganapathy | |
| 2011/0190807 A1 | 8/2011 | Redington et al. | |
| 2011/0238107 A1 | 9/2011 | Raheman | |
| 2011/0240043 A1 | 10/2011 | Redington | |
| 2011/0251635 A1 | 10/2011 | Caldarone | |
| 2012/0130419 A1 | 5/2012 | Leschinsky | |

FOREIGN PATENT DOCUMENTS

| | | |
|---|---|---|
| EP | 1016379 | 5/2000 |
| EP | 1 249 218 A2 | 10/2002 |
| GB | 1323365 | 7/1973 |
| JP | 2001221 A | 1/1990 |
| JP | 07-051276 | 2/1995 |
| JP | 2001505472 A | 4/2001 |
| JP | 2002539879 A | 11/2002 |
| RU | 2 253 429 C1 | 6/2005 |
| WO | WO 83/00995 A1 | 3/1983 |
| WO | WO 91/18571 | 12/1991 |
| WO | WO 98/30144 A1 | 7/1998 |
| WO | WO 00/57776 A1 | 10/2000 |
| WO | WO 2005/011503 A1 | 2/2005 |
| WO | WO 2005/077265 A1 | 8/2005 |
| WO | WO 2006/024871 A1 | 3/2006 |
| WO | WO 2006/030441 A2 | 3/2006 |
| WO | WO 2006/061825 A2 | 6/2006 |
| WO | WO 2007/085828 | 8/2007 |
| WO | WO 2008/148045 A1 | 12/2008 |
| WO | WO 2008/148062 A1 | 12/2008 |

OTHER PUBLICATIONS

Written Opinion from PCT Application No. PCT/US2012/033442, Jun. 12, 2012.

Ali et al., Remote ischemic preconditioning reduces myocardial and renal injury after elective abdominal aortic aneurysm repair: a randomized controlled trial. Circulation. Sep. 11, 2007;116(11 Suppl):I98-105.

Bartekova et al., Liver ischemia induced remote preconditioning: role of cardioprotective proteins. 25. ISHR-ES meeting. Jun. 21-25, 2005. Tromsoe, Norway. J Mol Cell Cardiol. 2005;38(6):1004.

Bøtker et al., Upper-limb ischemia during ambulance transfer reduces myocardial perfusion injury in STEMI. Heartwire. Mar. 28, 2009. Featured at i2 Session of AAC. Mar. 28-31, 2009. Last Accessed on Mar. 5, 2012 from http://www.theheart.org/article/951627.do.

Bøtker et al., Remote ischaemic conditioning before hospital admission, as a complement to angioplasty, and effect on myocardial salvage in patients with acute myocardial infarction: a randomised trial. Lancet. Feb. 27, 2010;375(9716):727-34.

Brzozowski et al., Ischemic preconditioning of remote organs attenuates gastric ischemia-reperfusion injury through involvement of prostaglandins and sensory nerves. Eur J Pharmacol. Sep. 19, 2004;499(1-2):201-13.

Cheung et al., Randomized controlled trial of the effects of remote ischemic preconditioning on children undergoing cardiac surgery: first clinical application in humans. J Am Coll Cardiol. Jun. 6, 2006;47(11):2277-82.

Dickson et al., Rabbit heart can be "preconditioned" via transfer of coronary effluent. Am J Physiol. Dec. 1999;277(6 Pt 2):H2451-7.

Dong et al., Limb ischemic preconditioning reduces infarct size following myocardial ischemia-reperfusion in rats] Sheng Li Xue Bao. Feb. 25, 2004;56(1):41-6. Chinese.

Gho et al., Myocardial protection by brief ischemia in noncardiac tissue. Circulation. Nov. 1, 1996;94(9):2193-200.

Hausenloy et al., Effect of remote ischaemic preconditioning on myocardial injury in patients undergoing coronary artery bypass graft surgery: a randomised controlled trial. Lancet. Aug. 18, 2007;370(9587):575-9.

Hausenloy et al., Preconditioning and postconditioning: underlying mechanisms and clinical application. Atherosclerosis. Jun. 2009;204(2):334-41. Epub Nov. 5, 2008.

(56) References Cited

OTHER PUBLICATIONS

Hausenloy et al., The therapeutic potential of ischemic conditioning: an update. Nat Rev Cardiol. Jun. 21, 2011;8(11):619-29.

Hoole et al., Cardiac Remote Ischemic Preconditioning in Coronary Stenting (CRISP Stent) Study: a prospective, randomized control trial. Circulation. Feb. 17, 2009;119(6):820-7. Epub Feb. 2, 2009.

Jenkins et al., Ischaemic preconditioning reduces troponin T release in patients undergoing coronary artery bypass surgery. Heart. Apr. 1997;77(4):314-8.

Kharbanda et al., Ischemic preconditioning prevents endothelial injury and systemic neutrophil activation during ischemia-reperfusion in humans in vivo. Circulation. Mar. 27, 2001;103(12):1624-30.

Kharbanda et al., Remote ischaemic preconditioning protects against cardiopulmonary bypass-induced tissue injury: a preclinical study. Heart. Oct. 2006;92(10):1506-11. Epub Jul. 3, 2006.

Kharbanda et al., Transient limb ischemia induces remote ischemic preconditioning in vivo. Circulation. Dec. 3, 2002;106(23):2881-3.

Konstantinov et al., Remote ischemic preconditioning of the recipient reduces myocardial ischemia-reperfusion injury of the denervated donor heart via a Katp channel-dependent mechanism. Transplantation. Jun. 27, 2005;79(12):1691-5.

Konstantinov et al., The remote ischemic preconditioning stimulus modifies inflammatory gene expression in humans. Physiol Genomics. Sep. 16, 2004;19(1):143-50. Epub Aug. 10, 2004.

Konstantinov et al., The remote ischemic preconditioning stimulus modifies gene expression in mouse myocardium. J Thorac Cardiovasc Surg. Nov. 2005;130(5):1326-32.

Lang et al., Myocardial preconditioning and remote renal preconditioning—identifying a protective factor using proteomic methods? Basic Res Cardiol. Mar. 2006;101(2):149-58. Epub Nov. 11, 2005.

Laskey et al., Frequency and clinical significance of ischemic preconditioning during percutaneous coronary intervention. J Am Coll Cardiol. Sep. 17, 2003;42(6):998-1003.

Leesar et al., Nonelectrocardiographic evidence that both ischemic preconditioning and adenosine preconditioning exist in humans. J Am Coll Cardiol. Aug. 6, 2003;42(3):437-45.

Leesar et al., Preconditioning of human myocardium with adenosine during coronary angioplasty. Circulation. Jun. 3, 1997;95(11):2500-7.

Loukogeorgakis et al., Remote ischemic preconditioning provides early and late protection against endothelial ischemia-reperfusion injury in humans: role of the autonomic nervous system. J Am Coll Cardiol. Aug. 2, 2005;46(3):450-6.

McCully et al., Adenosine-enhanced ischemic preconditioning: adenosine receptor involvement during ischemia and reperfusion. Am J Physiol Heart Circ Physiol. Feb. 2001;280(2):H591-602.

Murry et al., Preconditioning with ischemia: a delay of lethal cell injury in ischemic myocardium. Circulation. Nov. 1986;74(5):1124-36.

Nandagopal et al., Critical role for nitric oxide signaling in cardiac and neuronal ischemic preconditioning and tolerance. J Pharmacol Exp Ther. May 2001;297(2):474-8.

Peng et al., The protective effects of ischemic and calcitonin gene-related peptide-induced preconditioning on myocardial injury by endothelin-1 in the isolated perfused rat heart. Life Sci. 1996;59(18):1507-14.

Penttila et al., Ischemic preconditioning does not improve myocardial preservation during off-pump multivessel coronary operation. Ann Thorac Surg. Apr. 2003;75(4):1246-52; discussion 1252-3.

Peralta et al., Liver ischemic preconditioning: a new strategy for the prevention of ischemia-reperfusion injury. Transplant Proc. Aug. 2003;35(5):1800-2.

Przyklenk et al., Regional ischemic 'preconditioning' protects remote virgin myocardium from subsequent sustained coronary occlusion. Circulation. Mar. 1993;87(3):893-9.

Schmidt et al., Intermittent peripheral tissue ischemia during coronary ischemia reduces myocardial infarction through a KATP-dependent mechanism: first demonstration of remote ischemic perconditioning. Am J Physiol Heart Circ Physiol. Apr. 2007;292(4):H1883-90. Epub Dec. 15, 2006.

Schoemaker et al., Bradykinin mediates cardiac preconditioning at a distance. Am J Physiol Heart Circ Physiol. May 2000;278(5):H1571-6.

Tomai et al., Ischemic preconditioning in humans: models, mediators, and clinical relevance Circulation. Aug. 3, 1999;100(5):559-63.

Wolfrum et al., Calcitonin gene related peptide mediates cardioprotection by remote preconditioning. Regul Pept. Apr. 15, 2005;127(1-3):217-24.

Tejwani NC et al., "Tourniquet Cuff Pressure: The Gulf Between Science and Practice," J. Trauma, 61 (6), pp. 1415-1418, Dec. 2006. Product ad by Delfi Medical Innovations, Inc., (Delfi tourniquet)(2011).

Takarada et al., "Applications of Vascular Occlusion Diminish Disuse Atrophy of Knee Extensor Muscles," Official Journal of the American College of Sports Medicine, Medicine and Science in Sports and Exercise, pp. 2035-2039 (Apr. 2000).

May 29, 2013 Office Action from U.S. Appl. No. 13/542,929.

* cited by examiner

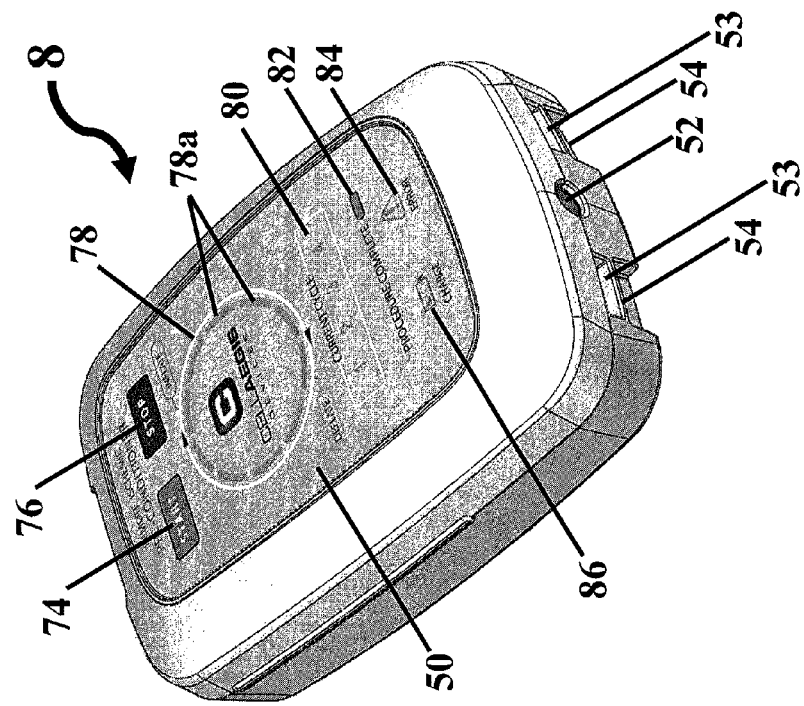
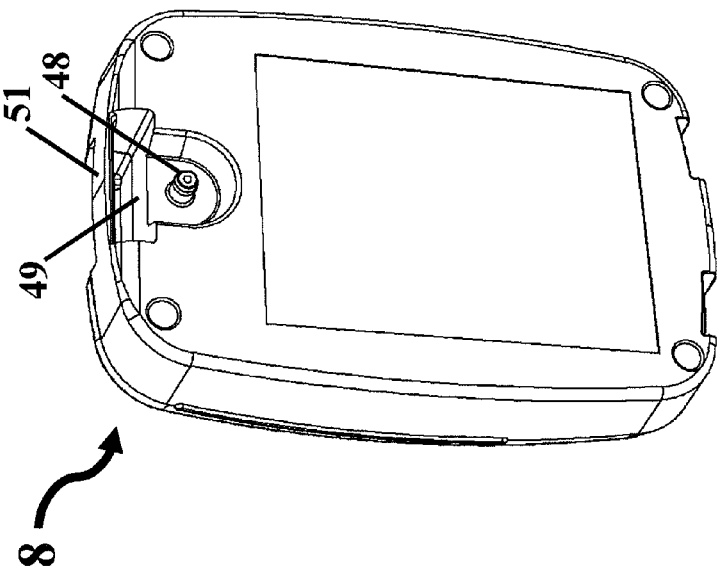
FIG. 8
FIG. 7

US 8,764,789 B2

SYSTEM FOR PERFORMING REMOTE ISCHEMIC CONDITIONING

FIELD

This invention relates generally to systems for performing remote ischemic conditioning, and more particularly, to systems for performing remote ischemic conditioning incorporating a removable controller.

BACKGROUND

Ischemic diseases are significant causes of mortality in industrialized nations. It is well established that tissue damage results from ischemia (insufficient blood flow to a tissue) followed by reperfusion (reflow of blood to the tissue). Ischemia and reperfusion cause disturbance of microcirculation with ensuing tissue damage and organ dysfunction. Organs such as the kidney, heart, liver, pancreas, lung, brain and intestine are known to sustain damage following ischemia and reperfusion.

In ischemic conditioning (IC), a tissue or organ or region of a subject's body is deliberately subjected to brief ischemic episodes, followed by brief reperfusion episodes. IC has been found to render the tissue, organ or region resistant to injury during subsequent ischemic episodes. The phenomenon of ischemic conditioning has been demonstrated in most mammalian tissues. IC is now recognized as one of the most potent innate protective mechanisms against ischemia-reperfusion (I-R) injury.

Remote ischemic conditioning (RIC) refers to the deliberate induction of transient ischemia in a subject at a region remote from at least some of the tissue to be protected. Often, RIC includes inducing transient ischemia in a subject's limb to protect organs remote from the limb, such as the myocardium. Myocardial protection has been demonstrated by a variety of remote stimuli, including renal ischemia, liver ischemia, mesenteric artery ischemia, and skeletal muscle hind limb ischemia.

RIC, in the broadest sense, involves deliberate induction of an ischemic period followed by a reperfusion period. The ischemic period may involve complete cessation of blood flow (blood flow occlusion). Such ischemic periods may be induced by applying super-systolic pressures on a region of the body, such as for example a limb. Alternatively, ischemic periods may also be induced by applying a less than systolic pressure.

RIC may be performed prior to (pre-), during (per-) and/or following (post-) an ischemic injury or other injury which benefits from RIC. RIC has shown benefit in reducing or preventing damage resulting from, myocardial infarction and trauma, inter alia,

SUMMARY

In one aspect, a device for performing RIC includes an inflatable cuff configured to encircle a limb of a subject and a controller removably attached to the cuff. The controller includes a pump; a manifold in fluid communication with the pump; an outlet in fluid to communication with the manifold and in removable fluid communication with the inflatable cuff; a pressure sensor; and a control circuit configured to implement a RIC treatment protocol.

In another aspect, a cuff assembly may be adapted to encircle a limb of a subject. The cuff assembly includes an inner layer, an outer layer, and a bladder disposed between the inner layer and the outer layer. The outer layer includes two flexible foam sections spaced apart in a longitudinal direction of the cuff assembly. The outer layer also includes an intermediate section disposed between the two flexible foam sections. The intermediate section may have a greater rigidity than the two flexible foam sections.

In a further aspect, a device includes an inflatable cuff and a controller attachment section. The inflatable cuff may be configured to encircle a limb of a subject. The cuff has an axial direction substantially parallel to an axis of the limb when the cuff is in the fitted state.

The controller attachment section may be operatively attached to the cuff by at least one attachment joint oriented substantially parallel to the axial direction of the cuff. The controller attachment section may include a connector adapted for removable attachment of a controller. The controller attachment section may provide fluid communication between the controller and cuff in a location removed from the connector when the controller is in an attached state.

It should be appreciated that all combinations of the foregoing aspects and additional concepts discussed in greater detail below (provided such concepts are not mutually inconsistent) are contemplated as being part of the inventive subject matter disclosed herein.

The foregoing and other aspects, embodiments, and features of the present teachings can be more fully understood from the following description in conjunction with the accompanying drawings.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. Various embodiments of the invention will now be described, by way of example, with reference to the accompanying drawings, in which:

FIG. 7 is a schematic bottom perspective view of the controller of the system depicted in FIG. 1;

FIG. 8 is a schematic top perspective view of the controller of the system depicted in FIG. 1;

DETAILED DESCRIPTION

The illustrative embodiments described herein are not necessarily intended to show all aspects of the invention. Aspects of the invention are not intended to be construed narrowly in view of the illustrative embodiments. It should be appreciated that the various concepts and embodiments introduced above and those discussed in greater detail below may be implemented in any of numerous ways, as the disclosed concepts and embodiments are not limited to any particular manner of implementation. In addition, it should be understood that aspects of the invention may be used alone or in any suitable combination with other aspects of the invention.

In one aspect, a system for performing RIC includes an inflatable cuff, a controller attachment section joined to the cuff, and a controller selectively removable from the controller attachment section. The controller may control the inflation and deflation of the inflatable cuff. Furthermore, the controller may include a control circuit programmed to implement an RIC protocol. In another aspect the cuff may be soft, rigid, and made from thermoformable materials.

Turning now to the figures, several possible embodiments are described in further detail.

Figure 1:
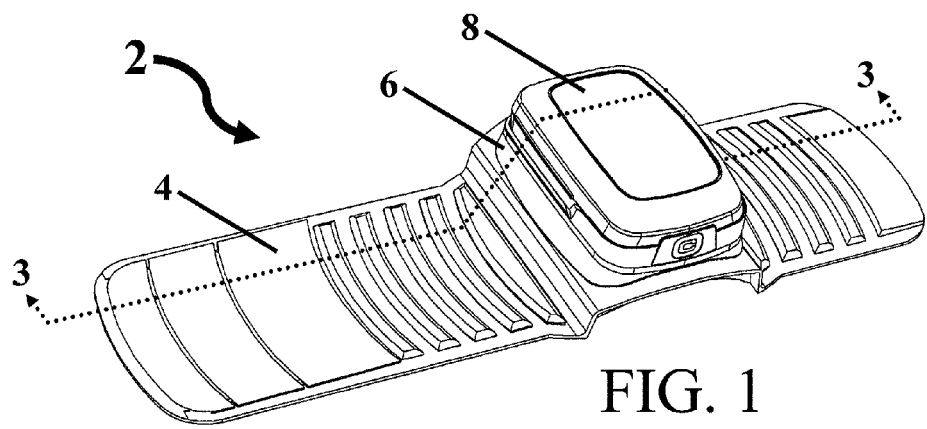
FIG. 1 is a schematic perspective view of an assembled system for remote ischemic conditioning with a removable controller.
Figure 2:
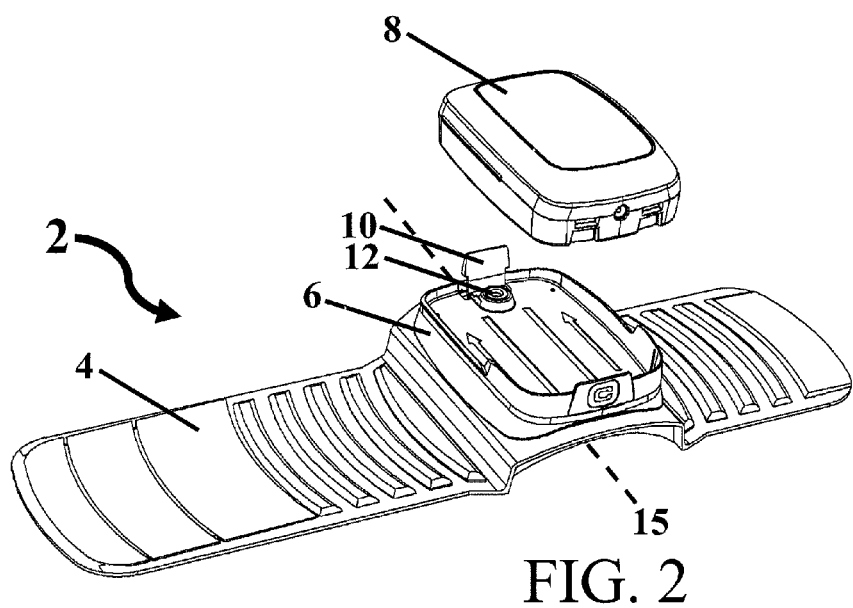
FIG. 2 is a schematic perspective view of the system for remote ischemic conditioning to depicted in FIG. 1 with the controller removed.

FIGS. 1 and 2 illustrate one embodiment of a system 2 for RIC. System 2 may include an inflatable cuff 4, a controller attachment section 6, and a controller 8. In some embodiments, as depicted in FIG. 2, the controller 8 is selectively removable from system 2. The controller attachment section 6 may include an interlocking retaining tab 10 adapted to provide removable attachment of the controller. The controller attachment section may also include a conduit 12 that provides, sealed, fluid communication between the controller 8 and inflatable cuff 6.

Figure 4:
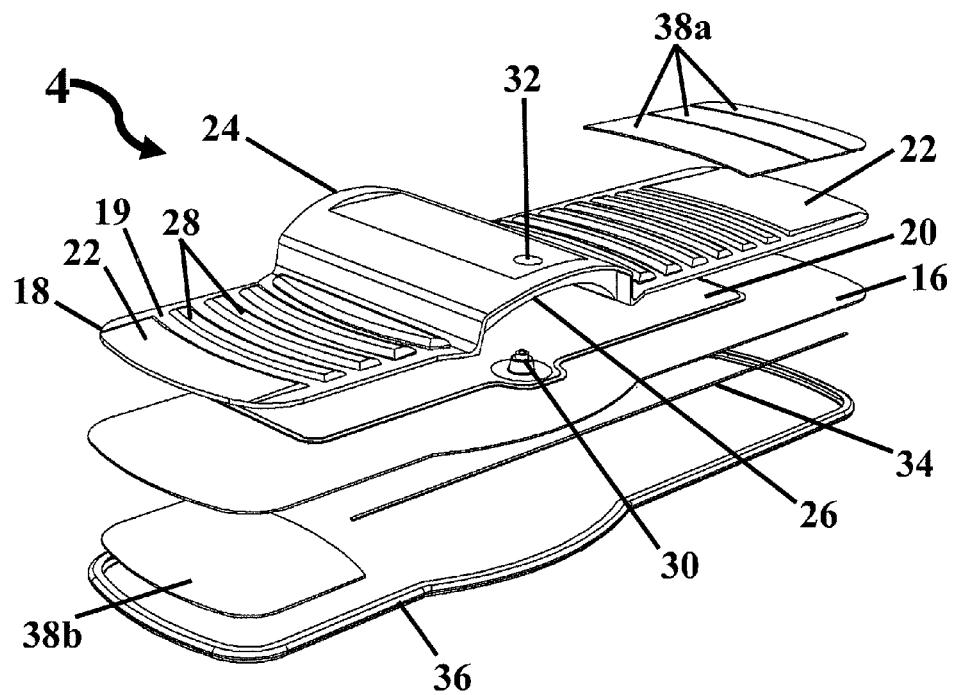
FIG. 4 is an exploded schematic perspective view of the cuff of the system depicted in FIG. 1.

In one aspect, cuff 4 is axially rigid while being soft or non-irritating to the skin. In one embodiment, cuff 4 may include an inner layer 16, a layer 18, and a selectively inflatable bladder 20 disposed between layers 16 and 18, as depicted in FIG. 4. Cuff 4 may be adapted to encircle a limb of an individual. Axis 15 represents the approximate center of a circular configuration formed when cuff 4 is wrapped about a patient's limb. An axial direction of cuff 4 corresponds to the approximate direction of axis 15. Cuff 4 has a longitudinal direction extending down the length of cuff 4 which is substantially perpendicular to the above defined axial direction. Cuff 4 may also be intended to be a disposable item for use with removable controller 8. Inner layer 16 typically is positioned adjacent to, and often in contact with, the skin of an individual wearing system 2. Since inner layer 16 may be in contact with skin, the inner layer may be made from a soft and/or non-irritating material. The inner layer 16 may be made from a knit, woven, or felted cloth. The cloth may include either natural or synthetic materials. Possible cloths include brushed polyester, brushed nylon, and/or other suitable materials as would be apparent to one of skill in the art. Alternatively, inner layer 16 may be made from a foam. In some embodiments, inner layer 16 may be further adapted to provide moisture absorption, wicking, and/or breathability to cuff 4.

In some embodiments, cuff 4 may include two sections 22 spaced apart in a to longitudinal direction and an intermediate section 24 disposed between the sections 22. Intermediate section 24 may be constructed to have a greater rigidity than sections 22. The increased rigidity of the intermediate section 24 may be created either by an inherent material property difference, a difference in the physical construction (e.g. a thicker section and/or inclusion of reinforcing features), or both. In one embodiment, the intermediate section 24 may include a substantially flat outer surface 25 for attachment to the controller attachment section 6. Intermediate section 24 may also include an inner surface 26 which is curved in the longitudinal direction of the cuff 4. The curved inner surface 26 may be constructed so as to generally conform to the curvature of a limb. In some embodiments, the size and curvature of the cuff 4 may be suited for a variety of sizes and ages of patients ranging from neonates to obese adults. The cuff 4 may also be sized for either attachment to an arm or a leg. The intermediate section 24 may be constructed from thermosetting plastics, thermoforming plastics, and/or foamed materials. Sections 22 and the intermediate section 24 may be integrally formed with one another, or they may be formed separately and subsequently joined using any appropriate method including, but not limited to, a sewn seam, ultrasonic welds, adhesives, rivets, clamping structures, and/or mechanically interlocking features. Section 22 may be formed of a foam material or any other suitably flexible yet strong material.

In one embodiment, cuff 4 may also include a plurality of reinforcing structures 28 substantially aligned in the axial direction of the cuff assembly. Reinforcing structures 28 typically may be formed in outer layer 18 of sections 22. Reinforcing structures 28 provide axial rigidity to the cuff 4. The increased axial rigidity provided by reinforcing structures 28 helps to distribute the pressure applied by cuff 4 in the axial direction to provide a substantially uniform pressure across the axial width of the cuff 4. Reinforcing structures 28 may also help to prevent kinks in cuff 4 when it is placed around the arm or leg of an individual. Reinforcing structures 28 may be spaced apart in a longitudinal direction to permit the cuff 4 to easily bend around an encircled limb while still providing increased axial rigidity. Reinforcing structures 28 may be curved or straight in shape in the axial direction. In some embodiments, the reinforcing structures 28 may be integrally formed with the foam in sections 22 such as by the application of heat and/or pressure (e.g. thermoforming) to selectively melt and/or compress portions of the foam in sections 22. The uncompressed and/or unmelted portions of foam in sections 22 form the raised reinforcing structures 28. Alternatively, reinforcing structures 28 may be separately formed and subsequently joined to sections 22.

Layer 18 may also include a cloth layer 19 applied to an exterior surface. Cloth layer 19 may be formed of a low stretch or non-stretch cloth. The low stretch or non-stretch properties may be an inherent property of the cloth selected. Alternatively, cloth layer 19 may be a made from thermoformable materials and may be laminated to the exterior surface of layer 18. The lamination process may alter the thermoformable fabric to be a low stretch or non-stretch material. In one embodiment, the cloth may be applied to and laminated with layer 18 in a flat layout prior to forming reinforcing structures 28. Reinforcing structures 28 may subsequently be thermoformed to a final desired shape. The resulting sections 22 may be soft and have low stretch or non-stretch properties. Furthermore, sections 22 may be thermoformable enabling subsequent processing steps.

Selectively inflatable bladder 20 may be disposed between inner layer 16 and layer 18. Bladder 20 may have a valve 30 arranged and adapted to provide a fluid inlet to the interior of bladder 20. Valve 30 extends through a hole 32 in the intermediate section 24 of cuff 4. Valve 30 may be placed in sealed fluid communication with a corresponding structure 33 on controller attachment section 6 which may also be in sealed fluid communication with an outlet 48 of controller 8. When connected to outlet 48 of controller 8 through structure 33 of the controller attachment section 6, valve 30 may provide pressurized gas such as air to bladder 20. In some embodiments, bladder 20 may be a component separate from layers 16 and 18. Bladder 20 may be formed such as by bonding two separate sheets of thermoplastic polyurethane together. In other embodiments, bladder 20 may be formed from air impermeable layers incorporated into layers 16 and 18 of cuff 4. Layers of bladder 20 may be bonded together in an air tight manner using any number of methods including adhesives, ultrasonic welding, beads of material around the edges, and/or other appropriate methods as would be apparent to one of skill in the art. Bladder 20 may also be formed as a unitary structure without separate layers.

Layers 16, 18, 19, and bladder 20 of cuff 4 may be held together at their edges in any suitable fashion, such as by a binding material 36 wrapped around the edge of cuff 4 and sewn to cuff 4, as shown in FIG. 4. Alternatively, cuff 4 may be held together using adhesives, rivets, ultrasonic welds, or other appropriate methods as would be apparent to one of skill in the art. In one aspect, it may be desirable to provide a non-slip interface to prevent cuff 4 from moving on the limb of a subject, since system 2 may be worn for protracted periods of time. To provide a non-slip interface, at least one non-slip structure 34 may be disposed on the face of inner layer 16. The non-slip structure 34 may be printed, glued, sewn, applied as a bead of material using a guided tool, or by hand. The non-slip structure 34 may include, but is not to limited to, one or more strips of silicone.

The cuff 4 may also include fasteners to hold the cuff on a limb of a subject and to adjust the circumferential size of the cuff 4 when in the fitted state. Such fasteners include, but are not limited to, hook and loop fasteners, latches, ratchet mechanisms, clasps, snaps, buckles, and other appropriate structures as would be apparent to one of skill in the art. For example, the fastener may be a hook and loop fastener including a plurality of adjacent unconnected hook sections 38a disposed on layer 18 or 19 and loop sections 38b disposed on inner layer 16. Hook sections 38a may extend in the axial direction of the cuff 4. The width of each hook section 38a, with respect to the longitudinal direction of the cuff, may be selected to provide a flexible cuff able to wrap around different sized limbs.

Figure 3:
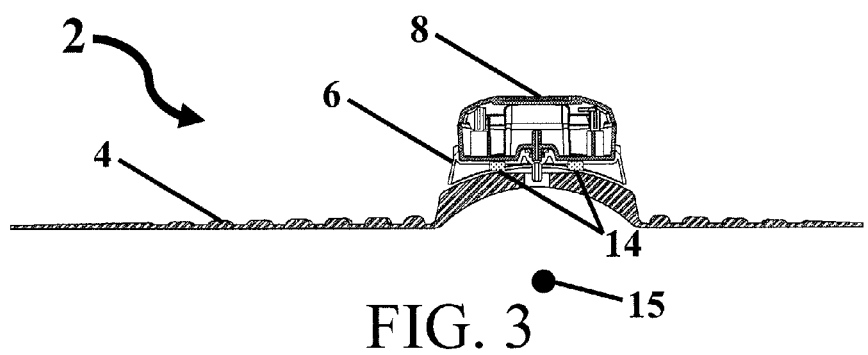
FIG. 3 is a cross sectional view of the system for remote ischemic conditioning depicted in FIG. 1 taken along the line 3-3 in FIG. 1.
Figure 5:
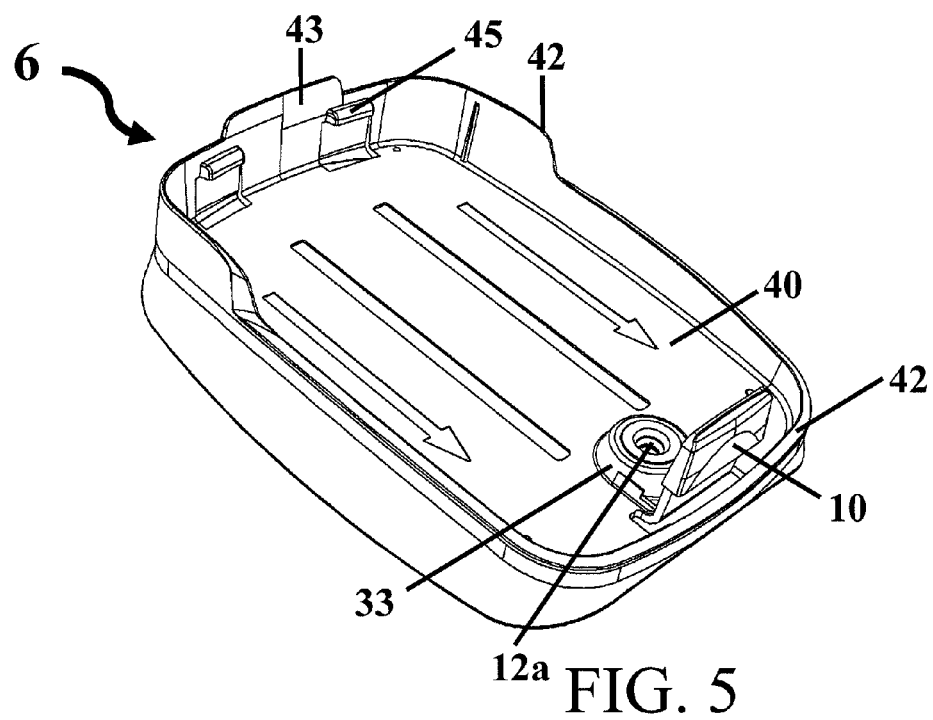
FIG. 5 is a schematic top perspective view of the controller attachment section of the system depicted in FIG. 1.
Figure 6:
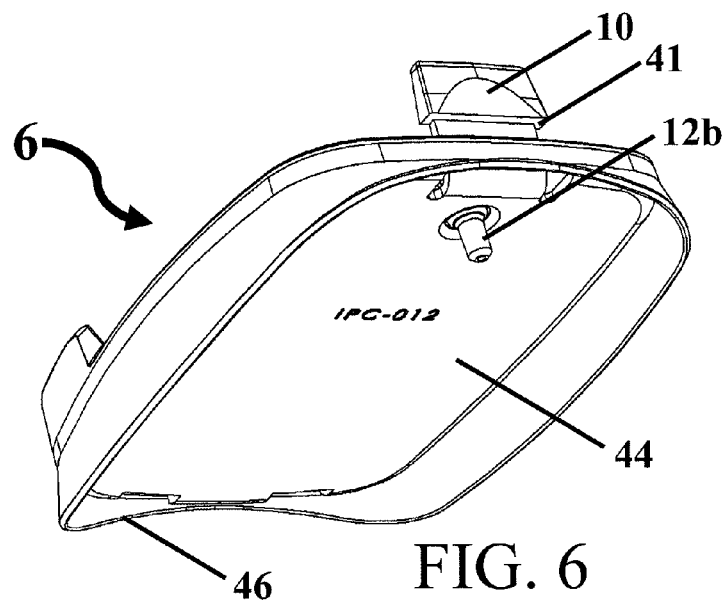
FIG. 6 is a schematic bottom perspective view of the controller attachment section of the system depicted in FIG. 1.

The controller attachment section 6 of FIG. 1 is shown in more detail in FIGS. 3, 5 and 6. In one embodiment, controller attachment section 6 may include an upper surface 40 for supporting controller 8 in the attached state, a lower surface 44, and an upstanding wall 42 surrounding surface 40. A raised portion 43 of upstanding wall 42 may be located adjacent to and block a power inlet 52 of controller 8 in the attached state. By blocking access to power inlet 52 in the attached state, raised portion 43 may prevent use of the device while controller 8 is connected to an external power source. The controller attachment section 6 may also include a connector, such as retaining tab 10, arranged to provide removable attachment of controller 8. In one embodiment, tab 10 is mounted at one end to surface 40 and includes a projecting edge 41 spaced from surface 40 that faces outwardly towards wall 42. Bosses 45 are disposed on wall 42 on the opposite side of section 6 from tab 10. When controller 8 is attached to attachment section 6, the upper portion of tab 10 is pushed inwardly away from wall 42 so that it passes through slot 49 that is disposed between the body of controller 8 and an outer band 51, as shown in FIG. 7. At the same time, bosses 45 extend into recesses 53 of controller 8, as shown in FIG. 8. Tab 10 has sufficient resilience that when snapped into place, this resilience creates an outward bias on tab 10 that causes edge 41 to overlie the upper edge of band 51. To release controller 8, the upper portion of tab 10 is again pushed inwardly against its bias toward controller 8 until edge 41 overlies slot 49 and is clear of band 51 at which time controller 8 may be pulled out of attachment section 6 at the end closest to tab 10.

In one embodiment, lower surface 44 and/or bottom edge 46 of controller attachment section 6 may be disposed on and substantially conform to the shape of an outer surface of cuff 4. In some embodiments, bottom surface 44 and/or bottom edge 46 of the controller attachment section 6 may be disposed on and substantially conform to the shape of outer surface 25 of intermediate section 24 of cuff 4 shown in FIG. 4. As shown in FIG. 3, the controller attachment section 6 may be joined to outer surface 25 of intermediate section 24 of inflatable cuff 4 along lower surface 44 by at least one and typically two attachment joints 14. In one embodiment, the attachment joint(s) 14 may be oriented substantially parallel to axis 15 of the cuff. The attachment joint 14 may be formed using any appropriate method including, but not limited to, a sewn seam, an ultrasonic weld, an adhesive, and/or rivets. When two or more attachment joints 14 are included, the joints 14 may be spaced apart in the longitudinal direction to allow the cuff 4 to bend and conform to the shape of different sized limbs.

Figure 9:
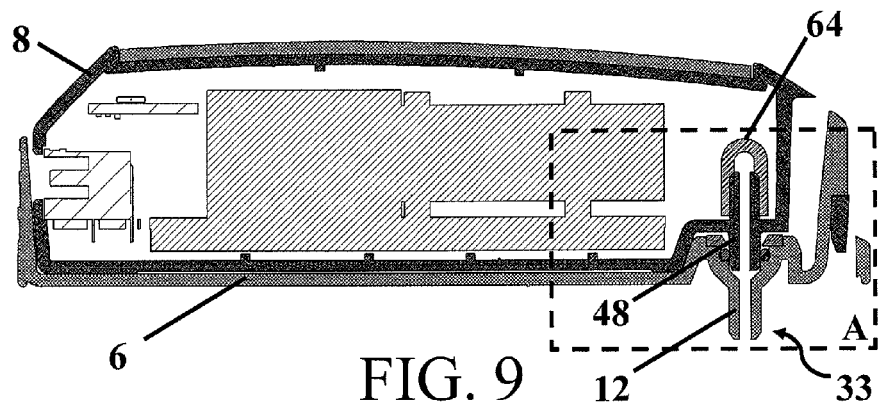
FIG. 9 is a cross sectional view of the controller and controller attachment section while coupled to the system depicted in FIG. 1.
Figure 9A:
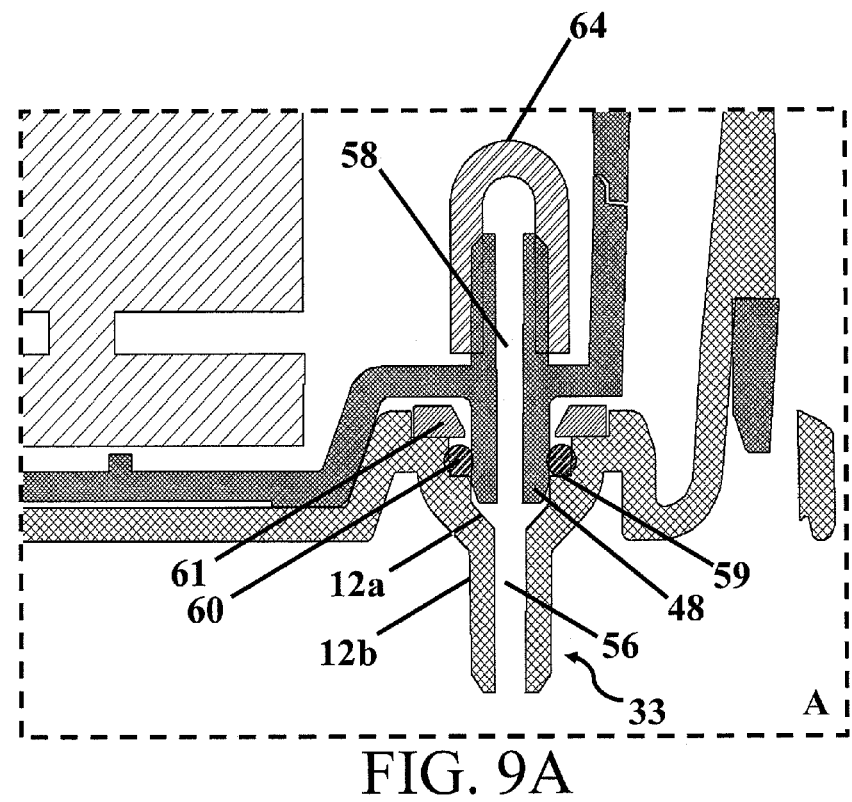
FIG. 9A is a detailed view of FIG. 9 corresponding to box A of FIG. 9.

As shown in FIGS. 9 and 9A, controller attachment section 6 may provide fluid communication between the controller 8 and bladder 20 of cuff 4 via structure 33. Structure 33 may include a conduit 12 which is provided in a location spaced from retaining tab 10, when the controller 8 is in an attached state. Conduit 12 fluidly couples controller 8 to valve 30 of bladder 20. Conduit 12 may include a female section 12a that is constructed and arranged to mate with an outlet 48 of controller 8 and a male section 12b that is constructed and arranged to mate with valve 30 of bladder 20. While a male and female connection have been described, the male and female portions could be reversed or even replaced with other comparable fluid connections, such as a tube or the like. A seal, such as O-ring 60, may be disposed on a shoulder 59 located in structure 33. The O-ring 60 may create a gland seal between female section 12a and outlet 48. Alternatively, a compression seal with O-ring 60 may be used. A retaining structure 61 may be included in structure 33 to retain O-ring 60. Retaining structure 61 may be joined to structure 33 using any appropriate method including, but not limited to, press fitting, ultrasonic welding, and/or adhesives.

Figure 10:
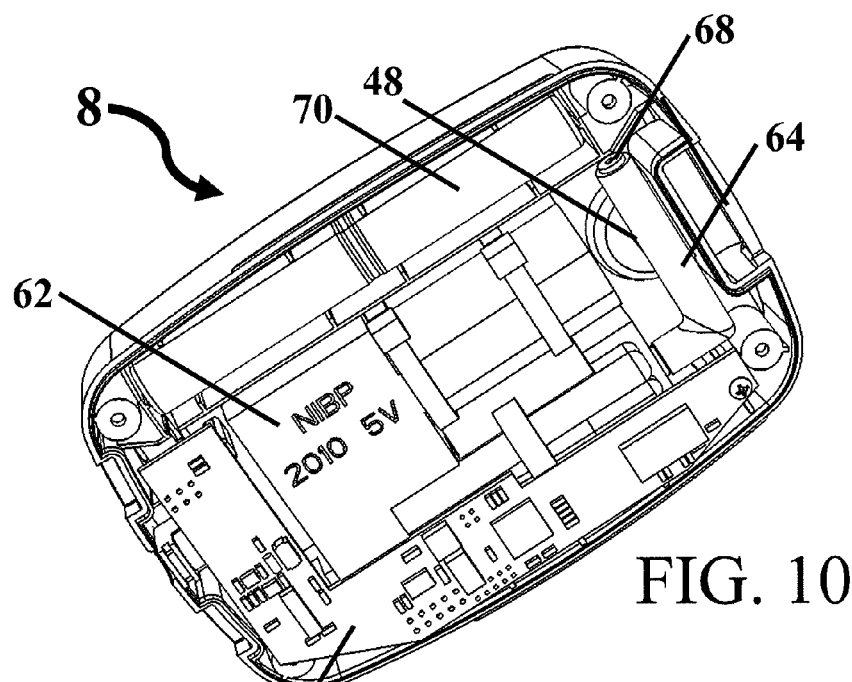
FIG. 10 is a schematic perspective view of the controller of the system depicted in FIG. 1 with the cover removed.
Figure 11:
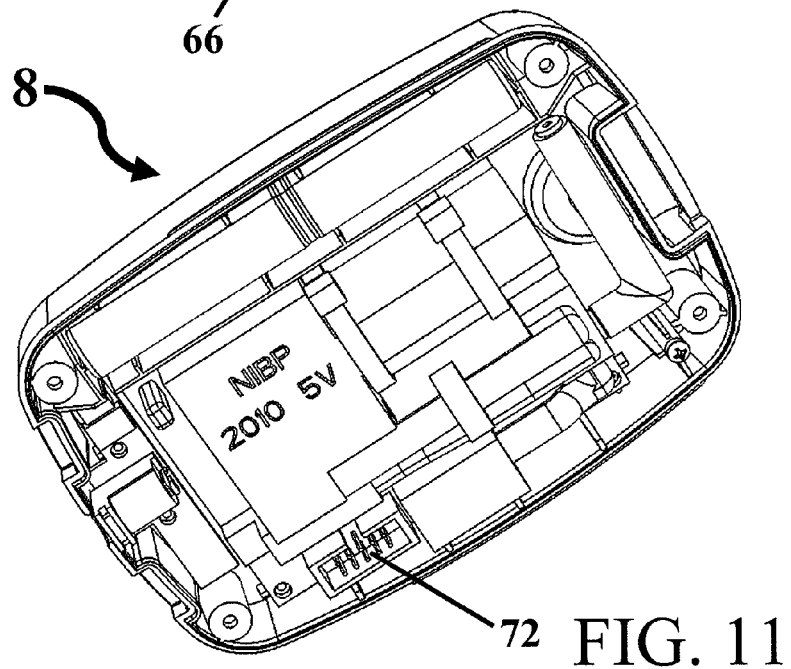
FIG. 11 is a schematic perspective view of the controller of the system depicted in FIG. 1 with the cover and PCB removed.

As shown in FIG. 8, controller 8 has a front cover 50, which may include controls and displays, and a power inlet 52. Guide structures 54 may be included in controller 8 for alignment and/or engagement with a charging mechanism The internal components of controller 8 are best shown in FIGS. 10 and 11, where front cover 50 of controller 8 has been removed. Controller 8 may include a pump 62 in fluid communication with a manifold 64. Manifold 64 is in fluid communication with relief valve 68 and outlet 48. Controller 8 may also include a printed circuit board (PCB) 66 which may include a control circuit and memory. The controller 8 may also include a pressure sensor associated with the pressurized components of the system and the control circuit. The pressure sensor (not shown) may be incorporated into pump 62 and/or placed in pressure sensing communication with manifold 64. Furthermore, the pressure sensor may communicate with the control circuit of PCB 66. The control circuit may be programmed to implement an RIC treatment protocol. The controller may also determine blood pressure during, or as part of, an RIC treatment protocol. To provide convenient mobile usage of system 2, batteries 70 may be arranged, typically in series, to provide a higher operating voltage. Alternatively, batteries 70 may be in electrical communication with a transformer adapted to provide a higher operating voltage. In one embodiment, the operating voltage may be approximately 5 to 6 VDC. In other embodiments, the operating voltage may be approximately 12 VDC or any other appropriate voltage. As shown in FIG. 11, PCB 66 may be connected to the other controller components through plug connector 72.

The control circuit of PCB 66 may be programmed with certain error conditions which may cause the procedure to be aborted or which may cause an indication of the error to appear on a display or which can be used in other known ways. These error conditions may include, but are not limited to: the cuff is not pressurized within a predefined period, such as 20 seconds, 30 seconds, 40 seconds, 50 seconds, or one minute; there is no communication between pump 62 and PCB 66 upon start up; there is no communication between pump 62 and PCB 66 for more than a predefined period, such as two, three, four, or five seconds; multiple consecutive repumps are needed to maintain cuff pressure; pump 62 continues to run and does not respond to an abort signal after a predefined number of retrys, such as three, four, or five retrys; pressure in cuff 4 is not near zero gage pressure within a predefined period, such as 20 seconds, 30 seconds, 40 seconds, 50 seconds, or one minute after the end of an inflation cycle; pressure in cuff 4 is above a predetermined pressure such as 200, 220, 240 or 260 mmHg for longer than a predefined period, such as 5, 10, 20, or 30 seconds; and the pump 62 CPU does not wake up after a command is sent to it by the control circuit. The error condition may be cleared and/or the system may be reset such as by pressing a stop button 76 on the face of controller 8.

During usage, controller 8 may be attached to controller attachment section 6 to place controller outlet 48 into fluid communication with cuff 4. Pressurized gas may then be pumped through controller outlet 48 to inflate the cuff 4. The cuff pressure may be controlled by selectively opening valve 68 in response to a command from the control circuitry of PCB 66. In some embodiments, valve 68 may include a pressure safety relief feature that opens valve 68 in response to an over pressure event during an RIC treatment. In one embodiment, valve 68 opens when the pressure in cuff 4 exceeds 260 mmHg Valve 68 may open in response to either an error command from the control circuitry of PCB 66, or the valve 68 may include an automatically actuated mechanical system. Controller 8 may also include a slow continuous relief valve. Such a valve would continuously release gas from inflated bladder 20 at a selected rate lower than the rated flow rate of the pump 62. The slow continuous release of gas from bladder 20 could be used to deflate bladder 20 in case of a mechanism failure.

In some embodiments, the control circuit of PCB 66 may be programmable by a health professional and/or an end user according to a prescribed treatment protocol. Alternatively, the control circuit may only be programmed at the factory and may not be altered afterwards by the end user. The control circuitry may also include non-volatile memory for the logging and storage of treatment history. A health care professional may be able to access this memory to determine the treatment history of a patient and determine compliance with a prescribed treatment regime. In another embodiment, the controller may send this information via wireless, or hard wired, communication to a separate receiver for patient records, monitoring, or call center purposes. In one embodiment, controller 8 may include a start button 74 and stop button 76. In some embodiments, the start and stop buttons 74 and 76 may be incorporated into a single button. Controller 8 may also include a hard wired and/or emergency stop button and/or a quick release valve (not shown). In other embodiments, other controls may be included to allow expanded control of an RIC treatment.

In addition to controls, controller 8 may include displays related to the current cycle, the number of cycles left in a treatment, whether the treatment is completed, error signals, charge of the system, and other relevant information. In one embodiment, controller 8 may include a cycle time display 78. Cycle time display 78 may indicate the remaining portion of the inflation/deflation cycle by using illuminated indicators 78a arranged in a circular pattern corresponding to a full inflation/deflation cycle. Each indicator 78a of cycle time display 78 may correspond to a set fraction of the inflation/deflation cycle. When all of the indicators 78a of cycle time display 78 are illuminated, the inflation/deflation cycle is complete. Alternatively, the indicators 78a of cycle time display 78 may start a cycle fully illuminated and sequentially turn off as the cycle proceeds. When each indicator 78a of cycle time display 78 is dark, the particular inflation/deflation cycle is complete. While a circular display has been disclosed, cycle time display 78 could also be arranged in other linear, or non-linear, shapes corresponding to a full cycle. Controller 8 may also include a current cycle display 80, or a digital numeric display, indicating whether the current cycle is the first, second, third, or to other cycle. A procedure complete indicator 82 may be illuminated with a solid color or it may blink when the RIC treatment is complete to indicate the end of the procedure. An error display 84 may indicate when an error has occurred by blinking or being fully illuminated. Alternatively, error display 84 may blink in a preset pattern or display a particular color to indicate which error has occurred. A battery charge indicator 86 may indicate the approximate charge remaining in the batteries 70, and may also signal that that the remaining charge is only sufficient for one cycle by blinking.

The above described system may be used for implementing an RIC treatment. The treatment includes placing cuff 4 on a limb of a user and attaching controller 8 to controller attachment section 6 on cuff 4. A user may then press start button 74 to initiate the treatment. Once started the control circuitry of PCB 66 monitors the pressure sensor and turns pump 62 on to inflate the cuff 4. The pressure is then increased to a desired pressure, such as a blood flow occlusion pressure. In one embodiment, the control circuitry of PCB 66 maintains the cuff pressure between preselected pressure limits such as 200 mmHg to 210 mmHg In other embodiments, the control circuitry of PCB 66 may first determine a systolic blood pressure. After determining a systolic blood pressure, the control circuitry of PCB 66 may subsequently initiate the RIC treatment protocol with a desired pressure such as a pressure greater than the measured systolic blood pressure. Regardless of the specific pressure used, the pressure may be maintained for a selected ischemic duration. Ischemic durations may last on the order of seconds or minutes. After completing the ischemic duration, the controller may activate valve 68 to deflate cuff 4 and initiate the reperfusion duration. Reperfusion durations generally last for at least a minute, although shorter reperfusion durations may be used. After completion of the reperfusion duration another RIC cycle may be conducted. An RIC treatment may include a single cycle or multiple cycles. In one embodiment, an RIC treatment may include four cycles with ischemic durations of approximately 5 minutes, and reperfusion durations of approximately 5 minutes. At the end of the last cycle the cuff 4 may deflate within 30 seconds and the controller 8 may confirm a near zero gage pressure prior to shutting down.

Figure 12:
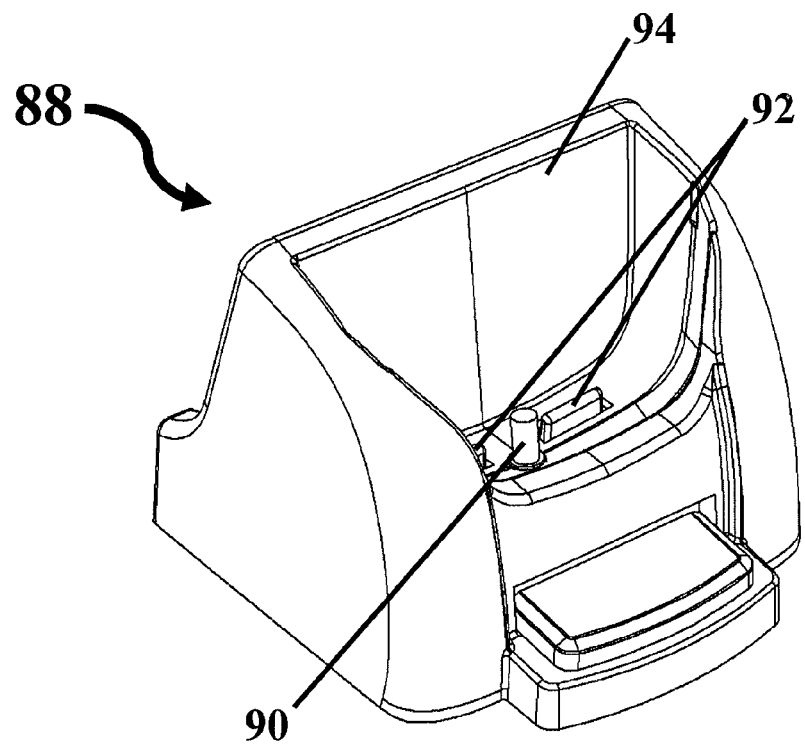
FIG. 12. is a schematic perspective view of a charging cradle to be used with the controller.
Figure 13:
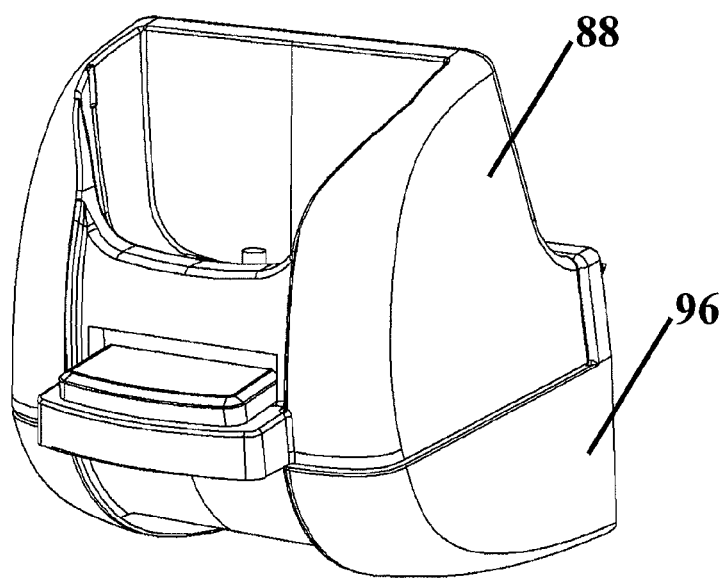
FIG. 13 is a schematic perspective view of the charging cradle of FIG. 12 with an optional wall mount.

In some embodiments, controller 8 may be charged using a charging cradle 88, as shown in FIG. 12. Charging cradle 88 may include a power connector 90 and mating guide structures 92. In one embodiment, mating guide structures 92 on the charging cradle mate with guide structures 54 on the controller. Mating guide structures 92 act as alignment features. In other embodiments, mating guide structures 92 may be actuated when controller 8 is inserted into the charging cradle 88 to turn the power on and off to power connector 90. Charging cradle 88 may also include a raised area 94 to prevent insertion of the controller while controller 8 is connected to cuff 4 or a patient. In addition to the above, charging cradle 88 may optionally connect with a wall mount portion 96 as shown in FIG. 13.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A device for remote ischemic conditioning comprising:
an inflatable cuff configured to encircle a limb of a subject;
a controller attachment section disposed on said cuff;
a controller having a body that is detachably attached to said controller attachment section, wherein said controller comprises:
a manifold configured to provide fluid communication between said controller and said cuff;
an outlet in fluid communication with said manifold and in removable fluid communication with said inflatable cuff; and
a control circuit configured to implement a remote ischemic conditioning treatment protocol;
wherein said controller includes a rechargeable battery and a power inlet configured for connection of said battery to a source of power to recharge said battery; and
wherein said controller attachment section further comprises an upstanding wall configured and arranged to block access to said power inlet on said controller when said controller is attached.

2. The device of claim 1, wherein said controller further comprises guide structures configured and arranged to mate with guide structures on a charging cradle, wherein said charging cradle includes a raised area configured and arranged to prevent insertion of said controller into said cradle when said controller is attached to said controller attachment section on said cuff.

* * * * *